(12) United States Patent
Renault

(10) Patent No.: US 7,071,167 B2
(45) Date of Patent: Jul. 4, 2006

(54) USE OF A COMBINATION OF COMPONENTS WITH AN INHIBITORY SYNERGISTIC EFFECT ON CALCIUM CHANNELS TO PREVENT OR TREAT WRINKLES AND FINE LINES

(75) Inventor: Béatrice Renault, Saint Maurice (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/705,857

(22) Filed: Nov. 13, 2003

(65) Prior Publication Data

US 2004/0147443 A1 Jul. 29, 2004

Related U.S. Application Data

(60) Provisional application No. 60/427,575, filed on Nov. 20, 2002.

(30) Foreign Application Priority Data

Nov. 13, 2002 (FR) .................................. 02 14183

(51) Int. Cl.
- *A61K 31/49* (2006.01)
- *A61K 38/08* (2006.01)
- *C07K 7/06* (2006.01)

(52) U.S. Cl. .................... 514/17; 514/557; 530/329
(58) Field of Classification Search ................ 530/300, 530/329, 350; 514/2, 12, 17, 21; 424/401, 424/78.03, 639, 681, 682, 697
See application file for complete search history.

(56) References Cited

U.S. PATENT DOCUMENTS 5,730,972 A * 3/1998 Simon et al. ................. 424/59
6,335,368 B1   1/2002 Liviero et al. .............. 514/561

(Continued)

FOREIGN PATENT DOCUMENTS

EP   1 088 548   4/2001
EP   1 180 524   2/2002

(Continued)

OTHER PUBLICATIONS

Blanes-Mira et al. A synthetic hexapeptide (Argireline) with antiwrinkle activity. International Journal of Cosmetic Science. 2002, vol. 24, pp. 303-310.*

(Continued)

*Primary Examiner*—Jeffrey Edwin Russel
(74) *Attorney, Agent, or Firm*—Finnegan, Henderson, Farabow, Garrett & Dunner, L.L.P.

(57) ABSTRACT

Disclosed herein is a composition for topical application to skin, comprising, in a physiologically acceptable medium (i) at least one peptide comprising at least one amino acid sequence derived from the amino acid sequence of the protein SNAP 25, and (ii) at least one calcium-channel inhibitor. Further disclosed is the use of this combination in a composition suitable for topical application to the skin, as an agent for preventing or treating wrinkles and fine lines, such as expression wrinkles, as well as a cosmetic treatment process comprising applying to the skin the composition.

21 Claims, 1 Drawing Sheet

U.S. PATENT DOCUMENTS

2002/0058682 A1     5/2002     Breton et al. ............... 514/354
2003/0235599 A1*   12/2003    Besne ....................... 424/401

FOREIGN PATENT DOCUMENTS

FR             2 793 681        11/2000
FR             2838344 A1 *   10/2003
WO        WO 94/26308      11/1994

OTHER PUBLICATIONS

Ji et al. Modulation of L-Type Ca2+ Channels by Distinct Domains Within SNAP-25. Diabetes. May 2002, vol. 51, No. 5, pp. 1425-1436.*

Ji et al. SNAP-25 inhibits L-type Ca2+ channels . . . Biochemical and Biophysical Research Communications. 2003, vol. 306, pp. 298-302.*

Wrinkle Cream Starts Stampede. Scotland on Sunday. Nov. 3, 2002. British Nursing News Online—News Archives [online], [retrieved on Mar. 2, 2005]. Retrieved from the Internet <URL: http://www.bnn-online.co.uk/news_datasearch . . . .*

DDF Wrinkle Relax (formerly Faux-Tox) by BeautyLand, copyright 2001 [online], [retrieved on Mar. 2, 2005]. Retrieved from the Internet <URL: http//www.beautyland.com/products/DDF/11997.asp.*

Skin Care Products Recommended by Dermatologists—DDF—Wrinkle Relax (aka Faux-Tox), [online], [retrieved on Mar. 2, 2005]. Retrieved from the Internet <URL: http://www.4derm.com/displaysingle.asp?criteria=12863&dr_id=1022BL.*

DDF Wrinkle Relax/Faux-Tox—cosmetic surgery news, copyright 2000-2005 [online], [retrieved on Mar. 2, 2005]. Retrieved from the Internet <URL: http://www.cosmeticsurgery-news.com/wrinkle_relax.html.*

* cited by examiner

SEQUENCE LISTING

<160> NUMBER OF SEQ ID NOS: 6

<210> SEQ ID NO 1
<211> LENGTH: 82
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

```
Ala Glu Asp Ala Asp Met Arg Asn Glu Leu Glu Glu Met Gln Arg Arg
 1               5                  10                  15

Ala Asp Gln Leu Ala Asp Glu Ser Leu Glu Ser Thr Arg Arg Met Leu
            20                  25                  30

Gln Leu Val Glu Glu Ser Lys Asp Ala Ile Arg Thr Leu Val Met Leu
        35                  40                  45

Asp Glu Gln Gly Glu Gln Leu Glu Arg Ile Glu Glu Gly Met Asp Gln
    50                  55                  60

Ile Asn Lys Asp Met Lys Glu Ala Glu Lys Asn Leu Thr Asp Leu Gly
65                  70                  75                  80
```

Lys Phe

```
<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Glu Met Gln Arg Arg
 1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Leu Glu Glu Met Gln Arg Arg Ala Asp Gln Leu Ala
 1               5                  10

<210> SEQ ID NO 4
<211> LENGTH: 86
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Asp Glu Arg Glu Gln Met Ala Ile Ser Gly Gly Phe Ile Arg Arg
 1               5                  10                  15

Val Thr Asn Ala Arg Glu Asn Glu Glu Met Asp Glu Asn Leu Glu Gln
                20                  25                  30

Val Ser Gly Ile Leu Gly Asn Leu Arg His Met Ala Leu Asp Met Gly
            35                  40                  45

Asn Glu Ile Asp Thr Gln Asn Arg Gln Ile Asp Arg Ile Met Glu Lys
        50                  55                  60

Ala Asp Ser Asn Lys Thr Arg Ile Asp Glu Ala Asn Gln Arg Ala Thr
 65                  70                  75                  80

Lys Met Leu Gly Ser Gly
                85

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ile Met Glu Lys Ala Asp Ser Asn Lys Thr Arg Ile Asp Glu Ala
 1               5                  10                  15

Asn Gln

<210> SEQ ID NO 6
<211> LENGTH: 19
<212> TYPE: PRT
```

```
-continued

<213> ORGANISM: Artificial Sequence
<220> FEATURE:
<223> OTHER INFORMATION: Description of Artificial Sequence: Synthetic
      peptide

<400> SEQUENCE: 6

Ala Asp Ser Asn Lys Thr Arg Ile Asp Glu Ala Asn Gln Arg Ala Thr
1               5                   10                  15

Lys Met Leu
```

USE OF A COMBINATION OF COMPONENTS WITH AN INHIBITORY SYNERGISTIC EFFECT ON CALCIUM CHANNELS TO PREVENT OR TREAT WRINKLES AND FINE LINES

This application claims benefit of U.S. Provisional Application No. 60/427,575, filed Nov. 20, 2002.

Disclosed herein is a composition that is suitable for topical application to skin, comprising, in a physiologically acceptable medium, (i) at least one peptide comprising at least one amino acid sequence derived from the amino acid sequence of the protein SNAP 25, and (ii) at least one calcium-channel inhibitor.

Women, and even men, currently have a tendency to wish to look youthful for as long as possible and consequently seek to fade out the signs of aging on the skin, which are reflected in particular by wrinkles and fine lines. In this respect, the media and the fashion world report about products intended to keep the skin radiant and wrinkle-free for as long as possible, which are signs of youthful skin, and all the more so since the physical appearance acts on the psyche and/or on the morale.

Up until now, wrinkles and fine lines have been treated using cosmetic products containing active agents acting on the skin, for example, by moisturizing it or by improving its cell renewal or alternatively by promoting the synthesis, or preventing the degeneration, of the elastic fibers which make up skin tissue.

Although these treatments make it possible to act on the wrinkles and fine lines caused by chronological or intrinsic ageing, and also on those caused by photo-ageing, they have no effect on expression wrinkles, which require an intervention on the contractile component of the wrinkles present in the skin.

Expression wrinkles are produced by mechanisms that differ from those generating lines due to ageing.

More precisely, expression wrinkles are produced by the stress exerted on the skin by the facial muscles which produce facial expressions. Depending on the shape of the face, the frequency of expressions and the existence of any tics, expression wrinkles can appear in childhood. Age and some environmental factors such as exposure to the sun do not have any effect on their genesis but can make them deeper and render them permanent.

Expression wrinkles are characterized by the presence of furrows at the periphery of the orifices, namely the nose (nasogenic furrows), the mouth (parabuccal lines and bitterness lines) and the eyes (crows feet) around which the facial muscles are located, and also between the eyebrows (glabellar lines or frown lines) and on the forehead.

Specifically, it has been shown that the facial skin muscles, in particular striated muscle fibers, which are under the direct control of the neuromuscular impulse, can play an essential role in the formation of expression wrinkles, and that modulating the neuromuscular impulse can attenuate expression wrinkles and also provide a "smoothing" effect on the skin's microrelief.

Moreover, it is believed that the phenotype of certain fibroblasts located along the tension lines created under the effect of contraction of facial muscles when making a facial expression is progressively modified under the effect of the contractions, endowing the fibroblasts, named myofibroblasts, with particular contractile properties related to striated muscle properties.

It is further known that the skin muscles of the face are under the control of motor nerve afferences of the facial nerve and that, moreover, the interlobular septa of the hypoderm contain within them fibers that constitute a striated muscle tissue. In the peripheral nervous system, the junction between a nerve and a striated muscle constitutes the neuromuscular plate, upstream of which is the afferent nerve pathway, known as the motor neuron. Moreover, cell membranes of each nerve fiber, and also of muscle cells, comprise numerous ion channels, and especially calcium channels, or chlorine channels, which can allow the controlled passage of $Ca^{2+}$ or $Cl^-$, respectively.

Variations in the intracellular $Ca^{2+}$ concentration are involved in initiating electrical and mechanical phenomena, for example, depolarization or contraction of smooth or striated muscle, hormonal secretion and activation of enzymes.

In particular, the increase in the calcium concentration is considered the cause of muscle contraction, and its decrease is considered to cause relaxation.

It is generally accepted that during the contraction phase, the thin actin filaments slide between the thick myosin filaments, thus resulting in shortening of the sarcomeres and consequently a contractile movement of the cell and of the fiber as a whole.

With respect to skeletal striated muscle, in the relaxed state, the actin is not accessible to the myosin bridges because it is associated with another protein complex consisting of troponin and myosin.

When calcium binds to the troponin-myosin complex, the actin molecules become accessible and the contractile phenomenon can then begin. The troponin molecule undergoes a conformational change that reveals the ATPase activity of the heads of the myosin molecule in the thick filaments, thus initiating contraction. The hydrolysis of the ATP to ADP and phosphate provides the chemical energy allowing the filaments to slide.

The role of $Ca^{2+}$ in the contractile proteins of striated muscle is thus an activating (de-inhibiting) role on the ATPase activity.

Relaxation of the striated muscle takes place when the transverse tubules and the cell membrane are repolarized, thus allowing the cellular intracytoplasmic $Ca^{2+}$ concentration to return to a value of $10^{-7}$ M, below the activation threshold of intracellular enzymes such as ATPase (activation threshold which is in the range of 1 to 2 concentration logarithms higher).

In the contraction of smooth muscle fibers, calcium is not an activator per se: it combines with calmodulin, and the calcium-calmodulin complex activates MLCK (myosin light chain kinase), forming therewith a ternary complex. This complex converts the myosin into phosphorylated myosin, which combines with actin, resulting in a contraction of the smooth fibers.

The contraction-relaxation cycle can be caused by variations in the cytoplasmic calcium concentration ranging from $10^{-7}$ M (inactive) to $10^{-5}$ M (active).

Regulating the intracellular cytoplasmic $Ca^{2+}$ concentration is only possible because the cytoplasmic calcium effluxes correct the cytoplasmic influxes. The intracytoplasmic $Ca^{2+}$ exchanges take place either with respect to intracellular storage vesicles or with respect to the exterior of the cell. In both cases, the $Ca^{2+}$ is not available in the cytoplasm. These exchanges can be ensured only by expelling intracellular cytoplasmic calcium via one or more "active" mechanisms capable of surmounting the electrochemical potential gradient mentioned above.

Two types of mechanisms can intervene: a calcium pump, which actively expels the cations at the expense of the hydrolysis of ATP, and a movement of $Ca^{2+}$ coupled to a movement of $Na^+$. In most cells, the ATP-dependent calcium pump operates more efficiently in the presence of calmodulin, which can increase its affinity.

In order to better describe the changes in permeability to calcium, it is currently common to consider that this permeability corresponds (i) to the opening of calcium channels that are dependent on the membrane potential, or voltage-operated channels (VOCs), which open during depolarization and allow calcium to enter the cell, or (ii) to the activation of membrane receptors.

Three types of VOCs are known: a channel that opens at a low potential, the T channel (Transient channel), and two types of channels that open at a high potential, the L channels (Long channels) and N channels (channels present in the neurons).

Moreover, it is very likely that these calcium channels show tissue specificity.

In 1965, T. Godfraind demonstrated that the permeability to calcium of the membrane might be inhibited by pharmacological agents, which would constitute the common mechanism on which $Ca^{2+}$ antagonists act.

It is thus understood from the text hereinabove that the contraction or hypercontraction of certain facial muscles, or of certain contractile cells of the dermis, for example, the myofibroblasts, which are assumed to be involved in the genesis of the expression wrinkles, may be induced by different mechanisms in particular those involving $Cl^-$, $Ca^{2+}$ and intracellular calcium ion exchanges, and that by acting in particular on the calcium channels, it is possible to relax these muscles or contractile cells and thus smooth out expression wrinkles.

So far, the means most commonly used for acting on expression wrinkles has been botulinum toxin, which is in particular injected into the wrinkles of the glabella, which are the wrinkles between the eyebrows (see J. D. Carruters et al., *J. Dermatol. Surg.* Oncol., vol.18, pp. 17–21 (1992)). Dermatologists also make use of degradable implants based on collagen, hyaluronic acid or polylactic acid.

However, these methods have the drawback of requiring a medical intervention and do not give long-lasting results.

There is thus a need for effective compounds that can be used in a composition suitable for topical application to the skin for preventing or treating, such as for smoothing out or fading out wrinkles and fine lines, for example, expression wrinkles.

The inventor has now discovered, surprisingly, that:

1) certain peptides have the effect of inhibiting type-L calcium channels, and that this effect can be observed on the three types of type-L calcium channels: DHP (dihydropyridine) site, diltiazem site and verapamil site; and 2) these peptides combined with magnesium can have synergistic antagonist effects with respect to the type-L calcium channels, verapamil site.

These type-L calcium channels were identified in human fibroblasts (Baumgarten, L. B. et al., *J. Biol. Chem.*, vol. 267, pp.10524–10530 (1992) and Chen, C. F. et al., *Science*, vol. 239, pp. 1024–1026 (1988)). The DHP, diltiazem and verapamil sites correspond to the sites on the type-L calcium channels that are specific for the corresponding pharmacological agents known as calcium inhibitors. Furthermore, depending on its affinity for certain calcium channels and for certain tissues, each calcium-inhibiting pharmacological agent can have a predominant effect corresponding to a preferential therapeutic indication.

Patent Application EP 1 180 524 discloses peptides with an anti-wrinkle effect, which, via a mechanism of inhibition of the SNARE complex (SNAP Receptor Complex), result in a reduction in the release of a neuromediator, acetylcholine, into the synaptic spaces.

The mechanism of action of these peptides is similar to that of botulinum toxins: they affect the formation and/or stability of the fusion protein complex (SNARE), which is a core of membrane proteins consisting of SNAP 25 (25 kDa Synaptosomal Associated Protein), syntaxin and synaptobrevin (or VAMP, for Vesicle-Associated Membrane Protein), the role of which is to mediate the neuronal exocytosis, i.e., the release of neurotransmitters (Ferrer Montier et al., *The Journal of Biological Chemistry*, vol. 272, pp. 2634–2638 (1997)).

However, no inhibitory activity on calcium channels is described or suggested for these peptides. In addition, it is not suggested to combine them with a calcium-channel inhibitor.

Moreover, the role of calcium, and of regulating its intracellular concentration, in muscle contraction/relaxation phenomena are known. It has previously been proposed to act on calcium channels in order to relax or decontract tissues, and thus reduce wrinkles and fine lines (FR-2 793 681).

However, no combination of (i) at least one peptide as defined below, and (ii) at least one calcium-channel inhibitor, has been previously proposed.

The inventor has now demonstrated that such a combination makes it possible to neutralize the formation of the expression wrinkles of the face: it can neutralize the effects of microtensions on the skin by relaxing the dermal contractile fibroblasts which are assumed to be involved in the genesis of expression wrinkles, and thus makes it possible to fade out expression wrinkles and to prevent them from deepening, while still allowing facial expressions.

Disclosed herein is thus a composition suitable for topical application to the skin, comprising, in a physiologically acceptable medium, (i) at least one peptide comprising at least one amino acid sequence derived from the amino acid sequence of the protein SNAP 25, and (ii) at least one calcium-channel inhibitor.

Figure 1:
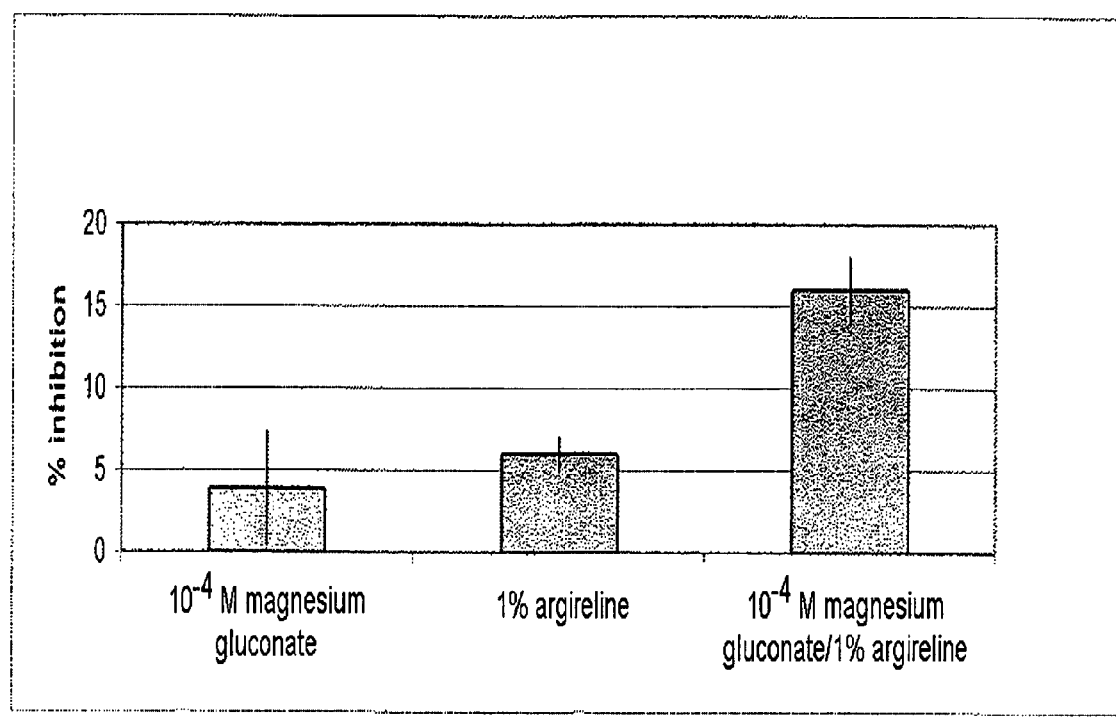
FIG. 1 is a histogram representing the effect of magnesium gluconate ($10^{-4}$ M) or of 1% Argireline® on calcium channels and the effect of their combination on type-L calcium channels, verapamil site, obtained from the results of Example 1 as disclosed herein.

As used herein, the term "sequence derived from the amino acid sequence of the protein SNAP 25" means any amino acid sequence or amino acid sequence fragment of the protein SNAP 25, defined by SEQ ID No. 1 or any amino acid sequence that differs from the sequence SEQ ID No. 1 by mutation, insertion, deletion or substitution of at least one amino acid, or by degeneracy of the genetic code, provided that it corresponds to a polypeptide having the activity of SNAP 25.

This peptide may have an amino acid sequence comprising from 3 to 30 amino acids such as from 6 to 19 amino acids, in which the N-terminal amino acid may be acetylated and/or the C-terminal amino acid may be amidated.

In one embodiment, a peptide that may be used is the hexapeptide defined by SEQ ID No. 2 (acetyl hexapeptide-3).

It is also possible to use a peptide chosen from:
(i) a peptide that is substantially homologous with the peptide defined by SEQ ID No. 2;
(ii) a peptide that is functionally equivalent to the peptide defined by SEQ ID No. 2;
(iii) a cosmetically acceptable salt of the peptide defined by SEQ ID No. 2; and
(iv) a peptide defined by SEQ ID No. 2 that has undergone reversible chemical changes.

The hexapeptide mentioned above is available from the company Lipotec under the trade name Argireline®: it comprises a sequence of 6 amino acids: glutamyl-glutamyl-methionyl-glutaminyl-arginyl-arginyl, wherein the first (N-terminal) amino acid is acetylated, and the last (C-terminal) amino acid is amidated.

As used herein, the term "substantially homologous" peptide or amino acid sequence means an amino acid sequence that is at least 60%, such as at least 80% and further such as at least 95% identical to the sequence SEQ ID No. 2.

As used herein, the term "percentage of identity" between two amino acid sequences is intended to mean a percentage of amino acid residues that are identical between the two sequences to be compared, obtained after the best alignment, wherein this percentage is purely statistical and the differences between the two sequences is distributed randomly and over their entire length. The terms "best alignment" and "optimum alignment" are intended to mean the alignment for which the percentage of identity determined as below is the highest. The sequence comparisons between two amino acid sequences are conventionally performed by comparing these sequences after they have been optimally aligned, wherein the comparison is performed by segment or by "window of comparison" to identify and compare the local regions of sequence similarity. The optimum alignment of the sequences for the comparison may be performed, other than manually, by means of the Smith-Waterman local homology algorithm (Ad. App. Math., vol. 2, p.482, (1981)), by means of the Neddleman-Wunsch local homology algorithm (J. Mol. Biol., vol. 48, p. 443 (1970)), by means of the Pearson-Lipman similarity search method (Proc. Natl. Acad. Sci. USA, vol. 85, p. 2444 (1988)) or by means of computer software using these algorithms (GAP, BESTFIT, BLAST P or BLAST N, available on the site NCBI, FASTA and TFASTA in Wisconsin Genetics Software Package, Genetics Computer Group, 575 Science Dr, Madison, Wis.). In order to obtain the optimum alignment, the BLAST program can, for example, be used, with the BLOSUM 62 matrix. The PAM or PAM2590 matrices may also be used.

The percentage of identity between two amino acid sequences is determined by comparing these two optimally aligned sequences in which the amino acid sequence to be compared may comprise additions or deletions relative to the reference sequence for an optimum alignment between these two sequences. The percentage of identity is calculated by determining the number of identical positions for which the amino acid residue is identical between the two sequences, dividing this number of identical positions by the number of compared positions, and multiplying the result obtained by 100 to obtain the percentage of identity between these two sequences.

The term "functionally equivalent peptide" means a peptide that has at least the capacity to inhibit type-L calcium channels.

The term "cosmetically acceptable salt of said peptide" means metal salts or salts formed by addition of suitable acids or bases, which may be obtained from a reaction with the peptides disclosed herein, according to the methods known to those skilled in the art.

Organic salts of peptides that may be mentioned include, for example, peptide gluconate, peptide acetate, peptide citrate, peptide oleate and peptide oxalate.

Mineral salts of peptides that may be mentioned include, for example, peptide chloride, peptide borate, peptide sulphate and peptide carbonate.

As "reversible chemical modifications" of the peptide so as to increase its bioavailability and its ease of passing through epithelial tissue without affecting its capacity to inhibit the type-L calcium channels, examples that may be mentioned include the esterification reaction of the carboxylate groups of the amino acids glutamic acid and aspartic acid with an acetylmethyl group, thus removing the negative charge from the amino acid and increasing its hydrophobicity.

These peptides may be obtained via conventional methods of chemical peptide synthesis or methods based on recombinant DNA technology, which are well known to those skilled in the art. For example, the solid-phase chemical synthesis method described by Pennington et al. (*Peptide synthesis protocols,* Humana Press, Totowa, (1994)) may be used.

It is also possible to use, in the context of the invention, at least one peptide chosen from:
a) a peptide comprising a sequence ranging from 3 to 30 amino acids contained in SEQ ID No. 1 (protein SNAP 25); for example, the peptide may comprise adjacent amino acids;
b) a peptide comprising a sequence ranging from 6 to 19 amino acids derived from the N-terminus of the protein SNAP 25, chosen from the peptides defined by SEQ ID No. 2 and SEQ ID No. 3;
c) a peptide comprising a sequence ranging from 6 to 19 amino acids derived from the C-terminus of the protein SNAP 25, chosen from the peptides defined by SEQ ID No. 5 and SEQ ID No. 6;
d) a peptide mixture comprising at least one peptide ranging from 3 to 30 amino acids chosen from those described in a), b) and c) and at least one peptide ranging from 3 to 30 amino acids contained in SEQ ID No. 4 ((COOH) peptide sequence); and
e) a peptide mixture comprising at least one peptide chosen from those formed by the peptides defined by SEQ ID No. 2 and SEQ ID No. 3 (N-terminus) and at least one peptide chosen from the peptides defined by SEQ ID No. 5 and SEQ ID No. 6 (C-terminus).

As disclosed herein, at least one of these peptides is combined with at least one calcium-channel inhibitor, the activity of which can be potentiated.

Two classes of active agents are known as calcium-channel inhibitors, respectively:
1) agents that are active on the plasma membrane, inhibiting the entry of calcium; and
2) agents that are active inside the cell (releasing intracellular reserves of $Ca^{2+}$, or inhibiting the formation of the $Ca^{2+}$ calmodulin complex).

In order for a substance to be recognized as a calcium-channel inhibitor, also referred to in the text as a calcium antagonist, it should be able to reduce the intracellular calcium concentration or to reduce the binding of calcium to intracellular proteins, such as calmodulin, as is described, for example, by Galizzi, J. P. et al., J. Biol. Chem., vol. 262, p. 6947 (1987), Okamiya, Y. et al., Eur. J. Pharmacol., vol. 205, p. 49 (1991), Wagner, J. A. et al., J. Neurosci., vol. 8, p. 3354(1988), Lee, H. R. et al., Life Sci., vol. 35, p. 721

(1984), Schoemaker H. and Lauger S., Eur. J. Pharmacol., vol.111, p. 273 (1985) or Reynolds, I. J. et al., J. Pharmacol. Exp. Ther., vol. 237, p. 731 (1986).

A substance is acknowledged as being relaxing when it shows a relaxing effect on contracted muscle tissue and/or shows an inhibitory effect in an experimental model of nerve-muscle junction (motor plate), for example, in the model described by W. Steinbrecher in: *Electrodes for stimulation and bioelectric potential recording*, Ed. Biomerstechnich, pages 96–98 (1988).

In one embodiment as disclosed herein, agents which are active on the plasma membrane, which inhibit the entry of calcium or which complex calcium, such as alverine and/or its organic or mineral salts, manganese and/or its organic or mineral salts or magnesium and/or its salts, can be used.

These compounds may be of natural or synthetic origin. The term "natural origin" means a compound in pure form or in solution, irrespective of its concentration in the solution, which may be obtained according to various extraction processes from a natural product. The term "synthetic origin" means a compound in pure form or in solution at any concentration, obtained by chemical synthesis.

Alverine and/or its organic or mineral salts may thus be used.

As organic alverine salts that may be used herein, mention may be made, for example, of alverine gluconate, alverine acetate, alverine citrate, alverine oleate and alverine oxalate.

Mineral alverine salts that may be mentioned include, for example, alverine chloride, alverine borate, alverine nitrate, alverine phosphate, alverine sulphate and alverine carbonate.

In one embodiment, the organic salt is alverine citrate and the mineral salt is alverine chloride.

It is also possible to use manganese, whether in ionic form or in salt form or in the form of natural, plant or microorganism extracts, such as bacterial extracts, which are rich in manganese.

Organic manganese salts that may be mentioned include, for example, manganese gluconate, manganese carbonate, manganese acetate, manganese citrate, manganese oleate and manganese oxalate.

Mineral manganese salts that may be mentioned include, for example, manganese chloride, manganese borate, manganese nitrate, manganese phosphate and manganese sulphate.

Needless to say, if a manganese-rich natural plant or microorganism extract, such as a bacterial extract, is used, a person skilled in the art knows how to adapt the amount of extract to be used in order finally to use the manganese in amounts that are suitable for the desired effect.

As manganese-rich natural extracts that may be used herein, mention may be made, for example, of extracts of walnut or extracts of tea.

In one embodiment, the calcium inhibitor used is magnesium or its salts.

The effects of magnesium, deduced, for example, from deficiency and overloading observations, are generally antagonistic to those of calcium. Magnesium is known to inhibit cationic channels, sodium channels and, for example, calcium-receptor and voltage-dependent channels, and behaves as an anti-calcium agent (M. L. Olinger, *Disorders of calcium and magnesium metabolism*, The Emergency Medicine Clinics of North America, Vol. 7, No. 4, November 1989).

Examples of magnesium salts that may be mentioned include magnesium sulphate, magnesium gluconate, magnesium aspartate, magnesium chloride and magnesium pidolate.

The amount of compounds that may be used herein depends on the desired effect, and may thus vary within a wide range.

To give an order of magnitude, the at least one peptide may be used in an amount ranging from 0.000001% to 1% by weight of the total weight of the composition such as from 0.00001% to 0.01% by weight of the total weight of the composition.

Similarly, it is possible to use the at least one calcium-channel inhibitor in an amount ranging from 0.0001% to 10% by weight of the total weight of the composition such as from 0.01% to 1% by weight of the total weight of the composition.

The composition disclosed herein is suitable for topical application to the skin and thus contains a physiologically acceptable medium, i.e., a medium that is compatible with the skin and optionally with its integuments (eyelashes, nails and hair) and/or mucous membranes.

This composition may be in any presentation form normally used in cosmetics, and it may, for example, be in the form of an optionally gelled aqueous solution, a dispersion of the lotion type, optionally a two-phase lotion, an emulsion obtained by dispersing a fatty phase in an aqueous phase (O/W emulsion) or conversely (W/O emulsion), or a triple emulsion (W/O/W or O/W/O emulsion) or a vesicular dispersion of ionic and/or nonionic type. These compositions are prepared according to the usual methods. In one embodiment, a composition in the form of an oil-in-water emulsion is used.

This composition may be more or less fluid and may have the appearance of a white or colored cream, an ointment, a milk, a lotion, a serum, a paste or a mousse. It may optionally be applied in the form of an aerosol. It may also be in solid form, such as in the form of a stick. It may be used as a care product and/or as a makeup product for the skin.

In a known manner, the composition disclosed herein may also comprise at least one adjuvant chosen from adjuvants that are common in cosmetics, such as hydrophilic and lipophilic gelling agents, hydrophilic and lipophilic active agents, preserving agents, antioxidants, solvents, fragrances, fillers, screening agents, pigments, odor absorbers and dyestuffs. The at least one adjuvant is present in an amount ranging, for example, from 0.01% to 20% by weight relative to the total weight of the composition. Depending on its nature, the at least one adjuvant may be introduced into the fatty phase, into the aqueous phase, or into lipid vesicles. In any case, these adjuvants, and also the proportions thereof, will be chosen so as not to harm the desired properties of the combination of anti-wrinkle active agents disclosed herein.

When the composition disclosed herein is an emulsion, the proportion of the fatty phase may range from 5% to 80% by weight such as from 5% to 50% by weight relative to the total weight of the composition. The oils, emulsifiers and co-emulsifiers used in the composition in emulsion form are chosen from those conventionally used in the field under consideration. The emulsifier and co-emulsifier are present in the composition in an amount ranging from 0.3% to 30% by weight such as from 0.5% to 20% by weight relative to the total weight of the composition.

As oils which may be used in the invention, mention may be made, for example, of mineral oils (liquid petroleum jelly or hydrogenated polyisobutene), oils of plant origin (avocado oil or soybean oil), oils of animal origin (lanolin), silicone oils (cyclomethicone or dimethicone) and fluoro oils (perfluoropolyethers). Fatty alcohols (cetyl alcohol), fatty acids and waxes (carnauba wax or ozokerite) may also be used as fatty substances.

As examples of emulsifiers and co-emulsifiers that may be used herein, mention may be made, for example, of fatty acid esters of polyethylene glycol such as PEG-100 stearate, and fatty acid esters of glycerol such as glyceryl stearate.

Hydrophilic gelling agents that may be mentioned include, for example, carboxyvinyl polymers (carbomer), acrylic copolymers such as acrylate/alkylacrylate copolymers, polyacrylamides, such as crosslinked polyacrylamido-methylpropane-sulphonic acid, polysaccharides, natural gums and clays, and lipophilic gelling agents that may be mentioned include, for example, modified clays, such as bentones, metal salts of fatty acids, hydrophobic silica and polyethylenes.

In one embodiment, the hydrophilic gelling agent for the composition disclosed herein is chosen from a crosslinked polyacrylamido-methylpropane-sulphonic acid as described in EP 0850642, WO9800094 or the Hostacerin AMPS commercialized by Clariant.

The composition disclosed herein may advantageously further comprise at least one compound as an active agent chosen from: desquamating agents; moisturizers; depigmenting and propigmenting agents; anti-glycation agents; NO-synthase inhibitors; agents for stimulating the synthesis of dermal or epidermal macromolecules and/or for preventing their degradation such as agents for stimulating the synthesis of epidermal macromolecules, such as an extract of beech buds (for example, the product sold by the company Gattefosse under the trade name Gatuline), agents for stimulating collagen synthesis, such as soybean protein hydrolysates (for example, the product sold by the company Coletica under the trade name Phytokine), agents for stimulating elastin synthesis and/or for inhibiting collagen degradation, such as an extract of the alga *Macrocystis pyrifera* (for example, the product sold by the company Secma under the trade name Kelpadelie) and agents for stimulating glycosaminoglycan synthesis, such as an extract of *Saccharomyces cerevisiae* (for example, the product sold by the company Cognis under the trade name Cytovitin); agents for stimulating fibroblast and/or keratinocyte proliferation or for stimulating keratinocyte differentiation, for example, a soybean protein extract such as the product sold by the company Cognis under the trade name Eleseryl; dermo-relaxants such as sapogenins and natural extracts, such as extract of Wild Yam; tightening agents such as polymers comprising a polysiloxane skeleton onto which are grafted mixed polymer units from the poly(meth)acrylic acid type and of the polyalkyl (meth)acrylate type, such as those sold by the company 3M under the trade names LO21 and VS80; antipollution agents and/or free-radical scavengers; agents that act on the capillary circulation; and agents that act on the energy metabolism of cells.

The compositions disclosed herein may also comprise at least one agent chosen from UVA-active and UVB-active organic and mineral photoprotective agents (absorbers), which are water-soluble or liposoluble, or even insoluble in the cosmetic solvents commonly used.

The organic photoprotective agents are chosen, for example, from anthranilates; cinnamic derivatives; dibenzoylmethane derivatives; salicylic derivatives; camphor derivatives; triazine derivatives such as those described in documents U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; $\beta,\beta,$-diphenylacrylate derivatives; benzotriazole derivatives; benzalmalonate derivatives; benzimidazole derivatives; imidazolines; bis-benzazolyl derivatives as described in documents EP 669 323 and U.S. Pat. No. 2,463,264; p-aminobenzoic acid (PABA) derivatives; methylenebis(hydroxyphenylbenzotriazole) derivatives as described in documents U.S. Pat. Nos. 5,237,071, 5,166,355, GB 2 303 549, DE 197 26 184 and EP 893 119; screening polymers and screening silicones such as those described, for example, in document WO 93/04665; dimers derived from x-alkylstyrene such as those described in document DE 198 55 649; 4,4-diarylbutadienes as described in documents EP 0 967 200, DE 197 46 654, DE 197 55 649, EP-A-1 008 586, EP 1 133 980 and EP 133 981, and mixtures thereof.

In one embodiment, the organic photoprotective agents are chosen from the following compounds: ethylhexyl salicylate, ethylhexyl methoxycinnamate, octocrylene, phenylbenzimidazolesulphonic acid, benzophenone-3, benzophenone-4, benzophenone-5,4-methylbenzylidenecamphor, terephthalylidenedicamphorsulphonic acid, disodiumphenyldibenzimidazoletetrasulphonate, 2,4,6-tris(diisobutyl 4'-aminobenzalmalonate)-s-triazine, anisotriazine, ethylhexyltriazone, diethylhexylbutamidotriazone, methylenebis (benzotriazolyl)tetramethylbutylphenol, drometrizole trisiloxane, 1,1-dicarboxy(2,2'-dimethylpropyl)-4,4-diphenylbutadiene, and mixtures thereof.

The mineral photoprotective agents are chosen from pigments and nanopigments (mean size of the primary particles generally ranging from 5 nm to 100 nm such as from 10 nm to 50 nm) of coated and uncoated metal oxides, for example, nanopigments of titanium oxide (amorphous or crystallized in rutile and/or anatase form), of iron oxide, of zinc oxide, of zirconium oxide or of cerium oxide, which are all UV-photoprotective agents that are well known per se. Standard coating agents are, for example, alumina and/or aluminium stearate. Such coated or uncoated metal oxide nanopigments are described, for example, in documents EP 518 772 and EP 518 773.

The photoprotective agents are generally present in the compositions disclosed herein in proportions ranging from 0.1% to 20% by weight relative to the total weight of the composition such as from 0.2% to 15% by weight relative to the total weight of the composition.

Further disclosed herein is the cosmetic use of at least one combination as described above, in a composition suitable for topical application to the skin, as an agent for smoothing out wrinkles and fine lines, such as expression wrinkles.

Even further disclosed herein is a cosmetic process for treating wrinkled skin, comprising topically applying to the skin a composition disclosed herein, for example, to the areas of the face or forehead marked with expression wrinkles and/or to individuals with expression wrinkles.

According to one embodiment, the composition is applied to the wrinkles and fine lines lying radially around the mouth and/or the eyes and/or horizontally on the forehead and/or in the space between the eyebrows.

The invention will now be illustrated with the non-limiting examples that follow. In these examples, the amounts are indicated as percentages by weight.

FIG. 1 is a histogram representing the effect of magnesium gluconate ($10^{-4}$ M) and of 1% Argireline® on calcium channels and the effect of their combination on type-L calcium channels, verapamil site obtained from the results of Example 1.

EXAMPLES

Example 1

Demonstration of an Inhibitory Effect of Argireline on Type-L Calcium Channels, and of an Inhibitory Synergistic Effect of the Argireline-magnesium Combination on Type-L Calcium Channels, Verapamil Site The test measured the capacity of a product to competitively inhibit the binding of type-L calcium-channel agonists.

The studies were performed using rat cerebral cortex homogenates (isolated membranes having type-L calcium channels at their surface).

The principle of an equilibrium displacement experiment includes measuring the specific binding at equilibrium, of a given concentration of radiolabelled ligand in the presence of a variable and increasing concentration of cold ligand. The cold ligand enters into competition with the radioactive ligand for its binding to the receptor; this is why this may be termed binding competition at equilibrium. This technique makes it possible:

to demonstrate that a cold ligand binds to a receptor, and
to study the binding of a ligand with weak affinity for a receptor.

The test products are listed in Table 1 below:

TABLE 1

| Compound | MW | Stock solution |
|---|---|---|
| 1% Argireline ® | | 100% (v/v) in water |
| $10^{-4}$ M magnesium sulphate or gluconate | 414.3 | $1 \times 10^{-2}$ M in water |
| Mixture of $10^{-4}$ M magnesium gluconate and 1% Argireline ® | | $1 \times 10^{-3}$ M in water |

The experimental conditions according to the protocol described by Reynolds, I. J. et al., *J. Pharmacol. Exp. Ther.*, vol. 237, p. 731 (1986) are presented in Table 2:

TABLE 2

| Test | Ligand | Concentration | Nonspecific | Incubation | Detection |
|---|---|---|---|---|---|
| $Ca^{2+}$ channel (L, verapamil site) | $(^3H)(-)$ D 888 | 0.5 nM | D 600 (10 μM) | 60 min/ 22° C. | Scintillation counting |

D 888 and D 600 are the reference molecules specific for the type-L calcium channels, verapamil site.

The specific binding of a ligand (labelled D 888) to the receptors (type-L calcium channels, verapamil site) is defined as the difference between the total binding and the specific binding determined in the presence of an excess of cold ligand. The results are expressed as a percentage of specific binding and as a percentage of inhibition of specific binding in the presence of the test compounds (Argireline®).

The results obtained for the verapamil site are given in Table 3 below and in the attached figure. The mean percentage of binding (%) and the mean percentages of inhibition are indicated.

TABLE 3

| Compounds | Concentration | % of binding | | | Mean % of binding | Mean % of inhibition |
|---|---|---|---|---|---|---|
| Argireline ® | 1.0% | 95.1 | 93.1 | 99.9 | 96.1 | 4 |
| Magnesium gluconate | $1 \times 10^{-4}$ M | 93.8 | 95.2 | 93.0 | 94.0 | 6 |
| Magnesium gluconate/ Argireline ® | $1 \times 10^{-4}$ M/ 1.0% | 81.6 | 85.3 | 85.1 | 84.0 | 16 |

The % of binding corresponds to the percentage of binding of the ligand in the presence of Argireline®, which acts as the competitor at the verapamil site.

These results thus show that Argireline® inhibits type-L calcium channels, verapamil site. The effect is observed mainly at the highest two concentrations, 5% and 10%, with mean percentages of inhibition of 36% and 52%, respectively. At a concentration of 1%, Argireline has a moderate effect (4%).

Magnesium gluconate used alone at concentrations of $1 \times 10^{-6}$ M to $1 \times 10^{-4}$ M has moderate effects on the type-L calcium channels, verapamil site. At the highest concentration, the mean percentage of inhibition is 6%.

Surprisingly, it is noted that the 1% Argireline®/$10^{-4}$ M magnesium gluconate combination has an inhibitory synergistic effect on type-L calcium channels, verapamil site. The effect represents a mean inhibition of 16%, i.e., an effect greater than the sum of the effects of each of the compounds.

Example 2

Formulation Examples

The following compositions were prepared in a conventional manner for those skilled in the art. The amounts indicated are percentages by weight.

| COMPOSITION 1: O/W EMULSION | | |
|---|---|---|
| Phase A | Water | qs 100% |
| | Preserving agents | 0.35% |
| | Manganese gluconate | 0.05% |
| Phase B1 | Silicone oils | 3% |
| | Cetyl alcohol and stearyl alcohol | 1.6% |
| | Hydrogenated polyisobutene | 4% |
| | Polyethylene glycol (100 EO) | 2% |
| Phase B2 | Volatile silicone oils | 3% |
| Phase D | Crosslinked polyacrylamido methylpropanesulphonic acid (Hostacerin AMPS from Clariant) | 1% |
| Phase E | Acetyl glutamyl-glutamyl-methionyl-glutaminyl-arginyl-arginylamide (SEQ ID No. 2) hexapeptide at 0.05% in water (Argireline from Lipotec) | 1% |

| COMPOSITION 2: W/O EMULSION | | |
|---|---|---|
| Phase A | Water | qs 100% |
| | Citric acid | 0.05% |
| | Preserving agents | 0.95% |
| | 50% sodium hydroxide | 2.98% |
| | Vinylpyrrolidone/styrene copolymer as a 40% emulsion | 3.34% |

| COMPOSITION 2: W/O EMULSION | | |
|---|---|---|
| | Fucose-rich polysaccharide at 1% in water (Fucogel from Solabia) | 2% |
| | Oxyethylenated (20 EO) sorbitan monolaurate | 1% |
| | Sodium citrate | 1.6% |
| | Magnesium gluconate | 0.05% |
| | Acetyl glutamyl-glutamyl-methionyl-glutaminyl-arginyl-arginylamide (SEQ ID No. 2) hexapeptide at 0.05% in water (Argireline from Lipotec) | 1% |
| Phase B | Oxyethylenated (18 EO) oxypropylenated (18 PO) mixture of cyclopentasiloxane and polydimethylsiloxane | 10% |
| | Cyclopentasiloxane | 8% |
| | Siloxane elastomer at 20% in polydimethylsiloxane (KSG-1 from Shin-Etsu) | 3% |
| Phase C | Acrylamide/sodium acrylamido-2-methylpropanesulphonate copolymer as a 40% inverse emulsion (Sepigel 305 from SEPPIC) | 2% |

| COMPOSITION 3: GEL | |
|---|---|
| Glycerol | 4% |
| Propylene glycol | 3% |
| Preserving agents | qs |
| Acrylamide/sodium acrylamido-2-methylpropanesulphonate copolymer as a 40% inverse emulsion (Sepigel 305 from SEPPIC) | 1.5% |
| Methacrylate copolymer powder | 1% |
| Alverine | 0.1% |
| Acetyl glutamyl-glutamyl-methionyl-glutaminyl-arginyl-arginylamide (SEQ ID No. 2) hexapeptide at 0.05% in water (Argireline from Lipotec) | 4% |
| Water | qs 100% |

| COMPOSITION 4: SERUM | |
|---|---|
| Sodium hydroxide | 0.1% |
| Tocopheryl acetate | 0.5% |
| Disodium salt of EDTA | 0.1% |
| Hydrogenated polyisobutene | 4.0% |
| Caffeine | 0.2% |
| Magnesium gluconate | 0.5% |
| Glycerol | 3.0% |
| Preserving agents | 1.2% |
| Cyclohexadimethylsiloxane | 6.0% |
| Crosslinked polyacrylamidomethyl-propanesulphonic acid (Hostacerin AMPS from Clariant) | 1.0% |
| Yeast extract | 0.3% |
| Acetyl glutamyl-glutamyl-methionyl-glutaminyl-arginyl-arginylamide (SEQ ID No. 2) hexapeptide at 0.05% in water (Argireline from Lipotec) | 1.0% |
| Citric acid | 0.1% |
| Tensioning agents | 7.0% |
| Water | qs 100% |

In each of the preceding formulations, the Argireline® may be replaced with one of the other peptides disclosed herein.

The above compositions are intended to be applied to the face in the morning and/or in the evening to correct expression wrinkles and fine lines and to relax the marks.

What is claimed is:

1. A composition for topical application to skin, comprising, in a physiologically acceptable medium, (i) at least one hexapeptide defined by SEQ ID No. 2 and (ii) magnesium gluconate.

2. The composition according to claim 1, wherein the at least one hexapeptide defined by the sequence SEQ ID No. 2 comprises a sequence of 6 amino acids of glutamyl-glutamyl-methionyl-qlutaminyl-arginyl-arginyl, wherein the first N-terminal amino acid is acetylated and the last C-terminal amino acid is amidated.

3. The composition according to claim 1, wherein the at least one hexapeptide defined by the sequence SEQ ID No. 2 is present in an amount ranging from 0.000001% to 1% by weight of the total weight of the composition.

4. The composition according to claim 3, wherein the at least one hexapeptide defined by the sequence SEQ ID No. 2 is present in an amount ranging from 0.00001% to 0.01% by weight of the total weight of the composition.

5. The composition according to claim 1, wherein the magnesium gluconate is present in an amount ranging from 0.0001% to 10% by weight of the total weight of the composition.

6. The composition according to claim 5, wherein the magnesium gluconate is present in an amount ranging from 0.01% to 1% by weight of the total weight of the composition.

7. The composition according to claim 1, further comprising at least one active agent chosen from desquamating agents; moisturizers; depigmenting and propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; dermo-relaxants; tightening agents; antipollution agents and free-radical scavengers; agents that act on the capillary circulation; and agents that act on the energy metabolism of cells.

8. The composition according to claim 1, further comprising at least one adjuvant chosen from hydrophilic and lipophilic gelling agents, hydrophilic and lipophilic active agents, preserving agents, antioxidants, solvents, fragrances, fillers, screening agents, pigments, odor absorbers and dyestuffs.

9. The composition according to claim 8, wherein the at least one adjuvant is present in an amount ranging from 0.01% to 20% by weight of the total weight of the composition.

10. The composition according to claim 1, wherein the composition is in a form chosen from an optionally gelled aqueous solution, a lotion dispersion, optionally a two-phase lotion, an O/W emulsion, an W/O emulsion, a triple emulsion chosen from W/O/W and O/W/O emulsions, and ionic and nonionic vesicular dispersions.

11. The composition according to claim 10, wherein the composition is in a form of an O/W emulsion.

12. The composition according to claim 1, further comprising at least one photoprotective agent chosen from UVA-active and UVB-active organic and mineral photoprotective agents.

13. The composition according to claim 12, wherein the at least one photoprotective agent is present in an amount ranging from 0.1% to 20% by weight of the total weight of the composition.

14. A method of making a cosmetic composition for topical application to skin, comprising including in the composition, as an agent for preventing or treating wrinkles and fine lines, (i) at least one hexapeptide defined by SEQ ID No. 2 and (ii) magnesium gluconate.

15. The method according to claim 14, wherein the prevention or treatment of wrinkles and fine lines comprises smoothing out the wrinkles and fine lines.

16. The method according to claim 14, wherein the wrinkles are expression wrinkles.

17. A cosmetic process for preventing wrinkles and fine lines on skin, comprising topically applying a composition to the skin, wherein the composition comprises, in a physiologically acceptable medium, (i) at least one hexapeptide defined by SEQ ID No. 2 and (ii) magnesium gluconate.

18. The cosmetic process according to claim 17, wherein the wrinkles are expression wrinkles.

19. A cosmetic process for treating wrinkled skin, comprising topically applying a composition to the skin, wherein the composition comprises, in a physiologically acceptable medium, (i) at least one hexapeptide defined by SEQ ID No. 2 and (ii) magnesium gluconate.

20. The process according to claim 19, wherein said composition is applied to the areas of the face or forehead marked with expression wrinkles and fine lines and/or to individuals with expression wrinkles and fine lines.

21. The process according to claim 19, wherein said composition is applied to the wrinkles and fine lines lying radially around the mouth and/or the eyes and/or horizontally on the forehead and/or in the space between the eyebrows.

* * * * *

UNITED STATES PATENT AND TRADEMARK OFFICE
CERTIFICATE OF CORRECTION

| | | |
|---|---|---|
| PATENT NO. | : 7,071,167 B2 | |
| APPLICATION NO. | : 10/705857 | |
| DATED | : July 4, 2006 | |
| INVENTOR(S) | : Béatrice Renault | |

It is certified that error appears in the above-identified patent and that said Letters Patent is hereby corrected as shown below:

Col. 17, lines 22-23, "glutamyl-glutamyl-methionyl-qlutaminyl-arginyl-arginyl," should read --glutamyl-glutamyl-methionyl-glutaminyl-arginyl-arginyl, --.

Signed and Sealed this

Seventh Day of November, 2006

JON W. DUDAS
*Director of the United States Patent and Trademark Office*